US00PP14857P2

(12) United States Plant Patent
Van Der Knaap

(10) Patent No.: US PP14,857 P2
(45) Date of Patent: Jun. 1, 2004

(54) SAINTPAULIA PLANT NAMED 'BUTTERFLY BLUE'

(50) Latin Name: *Saintpaulia ionantha*
Varietal Denomination: Butterfly Blue

(75) Inventor: Henricus G. J. Van Der Knaap, Honselersdijk (NL)

(73) Assignee: Kwekerij Mariënoord B.V., Honselersdijk (NL)

( * ) Notice: Subject to any disclaimer, the term of this patent is extended or adjusted under 35 U.S.C. 154(b) by 0 days.

(21) Appl. No.: 10/654,401

(22) Filed: Sep. 2, 2003

(51) Int. Cl.[7] ..... A01H 5/00
(52) U.S. Cl. ..... Plt./271
(58) Field of Search ..... Plt./271

*Primary Examiner*—Kent Bell
(74) *Attorney, Agent, or Firm*—C. A. Whealy

(57) ABSTRACT

A new and distinct cultivar of Saintpaulia plant named 'Butterfly Blue', characterized by its compact plant habit; freely flowering habit; and star-shaped double violet and light violet bi-colored flowers.

1 Drawing Sheet

Botanical classification/cultivar designation: *Saintpaulia ionantha* cultivar Butterfly Blue.

BACKGROUND OF THE INVENTION

The present invention relates to a new and distinct cultivar of Saintpaulia plant, botanically known as *Saintpaulia ionantha,* and hereinafter referred to by the name 'Butterfly Blue'.

The new Saintpaulia is a product of a planned breeding program conducted by the Inventor in Honselersdijk, The Netherlands. The objective of the breeding program was to create new Saintpaulia cultivars with double flowers and attractive flower coloration.

The new Saintpaulia originated from a cross-pollination made by the Inventor in July, 2000 in Honselersdijk, The Netherlands of a proprietary selection of Saintpaulia identified as code number E 55, not patented, as the female, or seed, parent with a proprietary selection of Saintpaulia identified as code number E 35, not patented, as the male, or pollen, parent. The new Saintpaulia was discovered and selected by the Inventor within the progeny of the stated cross-pollination in a controlled environment in Honselersdijk, The Netherlands.

Asexual reproduction of the new Saintpaulia by leaf cuttings taken since April, 2001 at Honselersdijk, The Netherlands, has shown that the unique features of this new Saintpaulia are stable and reproduced true to type in successive generations.

BRIEF SUMMARY OF THE INVENTION

The cultivar Butterfly Blue has not been observed under all possible environmental conditions. The phenotype may vary somewhat with variations in environment such as temperature, daylength and light intensity, without, however, any variance in genotype.

The following traits have been repeatedly observed and are determined to be the unique characteristics of 'Butterfly Blue'. These characteristics in combination distinguish 'Butterfly Blue' as a new and distinct cultivar:

1. Compact plant habit.
2. Freely flowering habit.

3. Star-shaped double violet and light violet bi-colored flowers.

Plants of the new Saintpaulia differ from plants of the female parent selection in flower form, shape and coloration.

Plants of the new Saintpaulia differ from plants of the male parent selection in flower size and coloration.

Plants of the new Saintpaulia can be compared to plants of the cultivar Rococo, not patented. In side-by-side comparisons conducted in Honselersdijk, The Netherlands, plants of the new Saintpaulia differed from plants of the cultivar Rococo in the following characteristics:

1. Plants of the new Saintpaulia were larger than plants of the cultivar Rococo.
2. Flowers of plants of the new Saintpaulia were positioned above the foliage whereas flowers of plants of the cultivar Rococo were occasionally within the foliage.
3. Flower color of plants of the new Saintpaulia was bi-colored whereas flower color of plants of the cultivar Rococo was not bi-colored.

BRIEF DESCRIPTION OF THE PHOTOGRAPHS

The accompanying colored photographs illustrate the overall appearance of the new Saintpaulia, showing the colors as true as it is reasonably possible to obtain in colored reproductions of this type. Colors in the photographs differ slightly from the color values cited in the detailed botanical description which accurately describe the colors of the new Saintpaulia.

The photograph at the top of the sheet comprises a side perspective view of a typical potted plant of 'Butterfly Blue'.

The photograph at the bottom of the sheet comprises a close-up view of the upper and lower surfaces of typical flowers of 'Butterfly Blue' (top) and upper and lower surfaces of typical leaves of 'Butterfly Blue' (bottom).

DETAILED BOTANICAL DESCRIPTION

In the following description, color references are made to The Royal Horticultural Society Colour Chart, 2001 Edition, except where general terms of ordinary dictionary significance are used. Plants used in the aforementioned photographs and for the following observations and measurements were grown in Honselersdijk, The Netherlands, during the spring under commercial practice in a glass-covered greenhouse for about 10 weeks in 12-cm containers. During the production of the plants, day and night temperatures averaged 22 and 19° C., respectively.

Botanical classification: *Saintpaulia ionantha* cultivar Butterfly Blue.

Parentage:

*Female, or seed, parent.*—Proprietary selection of *Saintpaulia ionantha* identified as code number E 55, not patented.

*Male, or pollen, parent.*—Proprietary selection of *Saintpaulia ionantha* identified as code number E 35, not patented.

Propagation:

*Type cutting.*—Leaf cuttings.

*Time to initiate roots, summer.*—About 20 days at 22° C.

*Time to initiate roots, winter.*—About 25 days at 22° C.

*Root description.*—Fine; well-branched; white in color.

Plant description:

*Form.*—Compact plant habit with rounded crown and outwardly spreading leaves. Plants are appropriate for 12-cm containers. Vigorous growth habit.

*Plant height at flowering.*—About 11 to 13 cm.

*Plant diameter at flowering.*—About 25 to 30 cm.

*Foliage description:*

*Arrangement.*—Simple, basal rosette.

*Length.*—About 7 to 10 cm.

*Width.*—About 4 to 9 cm.

*Shape.*—Broadly cordate.

*Apex.*—Acute.

*Base.*—Cordate, overlapping.

*Margin.*—Crenate.

*Texture, upper and lower surfaces.*—Pubescent.

*Venation pattern.*—Pinnate.

*Color.*—Developing foliage, upper surface: Darker than 147A. Developing foliage, lower surface: 59A. Fully expanded foliage, upper surface: Darker than 147A. Fully expanded foliage, lower surface: Closest to 191C overlain with 186A. Venation, upper surface: Darker than 147A. Venation, lower surface: 194A.

*Petiole.*—Length: About 6 to 8 cm. Diameter: About 6 to 8 mm. Texture, upper and lower surfaces: Pubescent. Color, upper and lower surfaces: 176B.

Flower description:

*Flower type and habit.*—Single star-shaped double flowers arranged in panicles that arise from the base; flowers face mostly upright. Freely flowering, about two to eight flowers per peduncle and about six to eight peduncles per plant. Flowers persistent. Flowers not fragrant.

*Natural flowering season.*—Plants flower year round in The Netherlands.

*Flower longevity.*—Flowers of plants of the new Saintpaulia maintain good substance for about seven to ten days under greenhouse conditions.

*Flower diameter.*—About 3.5 to 5 cm.

*Flower depth (height).*—About 1 to 1.5 cm.

*Flower buds.*—Shape: Spherical. Length: About 7 mm. Width: About 8 mm. Color: 79C.

*Petals.*—Quantity per flower: About 7 to 14. Length: About 1.2 to 2.5 cm. Diameter: About 1 to 1.6 cm. Shape: Ovate. Apex: Broadly acute. Margin: Entire; undulate, ruffled. Texture, upper and lower surfaces: Smooth, satiny. Color: When opening, upper surface: Darker than 86A; narrow 1 mm margin, 91C. When opening, lower surface: 79B; narrow 1 mm margin, 91C. Fully opened, upper surface: Closest to 89A; narrow 1 mm margin, 86D; main color becoming closer to 89B to 89C with development. Fully opened, lower surface: Closest to 88A; narrow 1 mm margin, 91B.

*Sepals.*—Quantity per flower: About five; fused. Length: About 8 mm. Diameter: About 2 mm. Shape: Ligulate. Apex: Acute. Margin: Entire. Texture, upper and lower surfaces: Smooth. Color, upper and lower surfaces: 177A.

*Peduncles.*—Length: About 6 to 8.5 cm. Diameter: About 3 to 5 mm. Angle: Mostly erect. Strength: Strong. Texture: Smooth. Color: Closest to 187C.

*Pedicels.*—Length: About 1.5 to 3 mm. Diameter: About 2 mm. Strength: Moderately strong. Texture: Smooth. Color: 187A.

*Reproductive organs.*—Stamens: Quantity per flower: About five. Anther length: About 2 mm. Anther color: 12A. Pollen: None observed. Pistils: Quantity per flower: One. Pistil length: About 1 cm. Style length: About 8 mm. Style color: 79B. Stigma color: 79A.

*Seed/fruit.*—Seed and fruit production has not been observed.

Disease/pest resistance: Plants of the new Saintpaulia have not been observed to be resistant to pathogens and pests common to Saintpaulias grown under commercial greenhouse conditions.

It is claimed:

1. A new and distinct cultivar of Saintpaulia plant named 'Butterfly Blue', as illustrated and described.

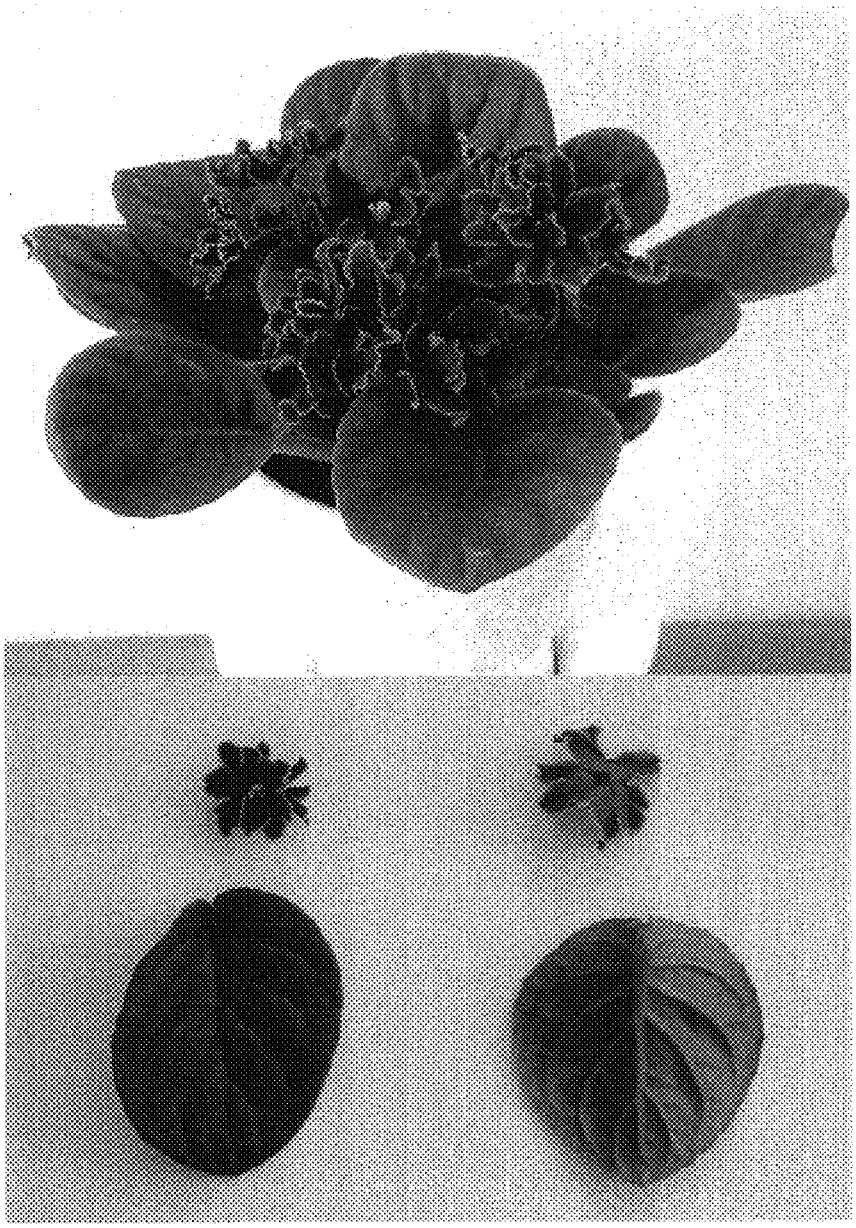

* * * * *